(12) United States Patent
Kellett et al.

(10) Patent No.: US 7,309,319 B2
(45) Date of Patent: Dec. 18, 2007

(54) APPARATUS AND METHOD FOR MEASURING THE DIMENSIONS OF THE PALPABLE SURFACE OF THE PROSTATE

(75) Inventors: Ian Peter Kellett, Salem, MA (US); John R. Erickson, Middleton, MA (US); Robert Schlesinger, West Sand Lake, NY (US)

(73) Assignee: Sensors for Medicine, Inc., Wayland, MA (US)

( * ) Notice: Subject to any disclaimer, the term of this patent is extended or adjusted under 35 U.S.C. 154(b) by 265 days.

(21) Appl. No.: 10/997,779

(22) Filed: Nov. 24, 2004

(65) Prior Publication Data

US 2006/0122538 A1    Jun. 8, 2006

Related U.S. Application Data

(60) Provisional application No. 60/524,552, filed on Nov. 24, 2003.

(51) Int. Cl.
*A61B 5/103* (2006.01)
(52) U.S. Cl. ........................ 600/587; 600/550
(58) Field of Classification Search ............... 600/587, 600/550
See application file for complete search history.

(56) References Cited

U.S. PATENT DOCUMENTS

| | | | | | |
|---|---|---|---|---|---|
| 5,423,332 | A | * | 6/1995 | Zirps et al. | 600/587 |
| 5,582,620 | A | * | 12/1996 | Hirsch | 606/192 |
| 5,867,831 | A | * | 2/1999 | Husain | 2/161.7 |
| 5,922,018 | A | | 7/1999 | Sarvazyan et al. | |
| 6,142,959 | A | | 11/2000 | Sarvazyan et al. | |
| 6,743,165 | B2 | * | 6/2004 | Mosel et al. | 600/30 |
| 2003/0210259 | A1 | * | 11/2003 | Liu et al. | 345/702 |

* cited by examiner

*Primary Examiner*—Max Hindenburg
*Assistant Examiner*—Emily M Lloyd
(74) *Attorney, Agent, or Firm*—George A. Herbster

(57) ABSTRACT

A method and system for measuring the dimensions of the palpable surface of the prostate in the physician's office and calculating prostate volume, rate of growth and changes in rate of growth. A membrane with a grid pattern is located proximate the prostate. A physician moves a measurement system, formed at the end of the index finger and located in a glove, between opposite margins of the prostate. The measurement system counts the grid elements between the margins that translate into a quantitative measurement of size of the palpable surface of the prostate.

9 Claims, 6 Drawing Sheets

US 7,309,319 B2

APPARATUS AND METHOD FOR MEASURING THE DIMENSIONS OF THE PALPABLE SURFACE OF THE PROSTATE

CROSS REFERENCE TO RELATED APPLICATION

This application claims priority from U.S. Provisional Application No. 60/524,552 filed Nov. 24, 2003 for Apparatus and Method for Measuring the Dimensions of the Palpable Surface of the Prostate.

BACKGROUND OF THE INVENTION

1. Field of the Invention

This invention relates generally to medical devices. It relates particularly to a method and system for use by a physician for measuring the palpable surface of the prostate thereto to determine the size and growth of the prostate and more specifically to a method and apparatus for the enabling trans-rectal measurement of the size, growth rate and changes in growth rate of the prostate during a standard digital rectal exam.

2. Description of Related Art

Prostate gland, or prostate, problems are widespread in the male population, especially the older male population. In particular, benign prostatic hyperplasia (BPH) and prostate cancer are common in men over 50 years of age. Indeed, prostate cancer is the second most common cancer in men in this country. Each year there are over 200,000 new cases and over 30,000 deaths. However, if prostate cancer is detected early and treated effectively, the chance of survival improves significantly. Unfortunately, conventional methods for detecting prostate problems are wanting as many early stage cancers go undetected.

In an attempt to enhance the efficiency and efficacy of methods and systems of detection of prostate cancer, medical science has used ultrasonics to diagnose prostate problems. Such systems are very expensive, and are not yet widely available in the urologist's or primary care physician's examining room. Most ultrasound imaging is performed by radiologists at an outside facility, or at the practitioner's office on a contract basis with a portable ultrasound unit. The technology and interpretation is difficult to master, requiring a time-consuming learning curve. Consequently, no routine examining system or technique exists which provides the high degree of accuracy in monitoring prostatic growth, nor is the required repeatability of results achieved.

Thus, the digital rectal examination continues to be the modality of choice for monitoring the prostate even though the process is very subjective. The standard exam is done by inserting a finger into the rectum and palpating or feeling the palpable surface of the prostate. The physical characteristics of the prostate size, contour, consistency, symmetry, presence or absence of the lateral margins, and the presence or absence of nodularity, are assessed and recorded by attempting to translate the physician's subjective impressions into a written record. This method of data collection is inexact and makes comparisons from exam to exam very difficult.

What is needed is a method and apparatus that overcomes these deficiencies by enabling the physician to monitor changes in the size of the palpable surface of the prostate for a given patient over time thereby to gauge more accurately changes in the size of the prostate.

SUMMARY

Therefore it is an object of this invention to provide a method and apparatus for facilitating examinations of the prostate.

Another object of this invention is to provide a method and apparatus for providing quantitative information concerning the size of the prostate.

Still another object of this invention is to provide a method and apparatus for providing repeatable quantitative information about the size of the prostate.

Yet another object of this invention is to provide a method and apparatus for examining the prostate that is simple to use.

Still yet another object of this invention is to provide a medical device for facilitating digital examination of a patient's prostate that provides repeatable quantitative information that is easy to use and that is readily manufactured.

Still yet another object of this invention is to provide a method of making accurate and repeatable quantitative measurements of the size of the palpable surface of the prostate thereby to establish a basis for calculating prostatic volume, rate of growth and changes in rate of growth, and a method for storing the resultant data in a database for subsequent recovery and comparison. It is used at the same time, and in conjunction with, a digital examination, allowing the physician to gather the traditional subjective data but with the added capability of accurate measurements of the prostate being palpated.

Still yet another object of this invention is to provide a method of measuring the size of the palpable surface of the prostate by placing a thin diaphragm upon which is printed a regular pattern, such as a calibrated grid, over the palpable surface of the prostate. The grid lines provide reference marks, which are detected by a photodetection device having a portion attached to the finger of the examining physician. The output of a photodetector associated with the photodetection device is connected via an interface circuit to a computing device, which counts the grid lines as the finger passes from one side to the other of the palpable surface of the prostate.

In accordance with one embodiment of this invention, a medical device for use by a physician during a digital measurement of the size of the palpable surface of a prostate includes an index finger structure for attachment to the end of the physician's index finger. A membrane overlies the physician's index finger and the attached index finger structure. The membrane proximate the index finger portion is stabilized proximate the prostate. A motion transducer attaches to the index finger structure and generates displacement signals in response to motion of the physician's index finger. A processor converts the displacement signals into a measurement of the size of the palpable surface of the prostate.

In accordance with another aspect of this invention a physician can measure changes in the size of a prostate by measuring the size of the palpable surface of the prostate during digital examinations. A closed volume is formed within the rectum proximate the prostate and about the physician's index finger. Motion of the physician's index finger is converted into displacement signals. Processing the displacement signals yields a measurement of the size of the palpable surface of the prostate that is a function of the size of the prostate.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
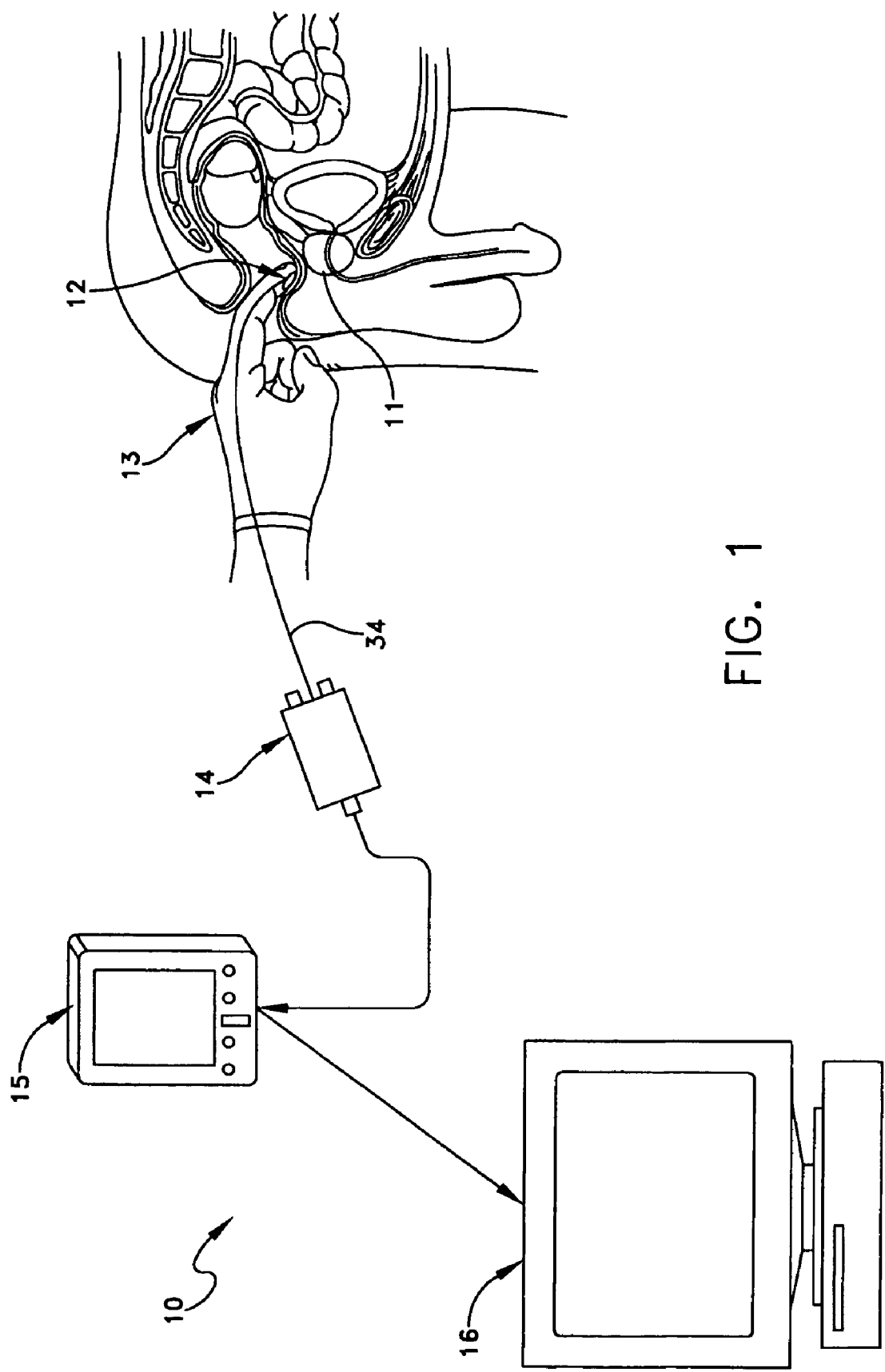
FIG. 1 is a schematic view of a prostate measurement system embodying this invention.

In FIG. 1 a system 10 in accordance with this invention provides a measurement indicative of prostate size. More specifically, a physician positions a sensor 12 in the rectum proximate to the prostate 11 during a standard digital rectal exam. The sensor 12 attaches to the physician's index finger and connects through an interface 14 to a computing device such as a personal digital assistant (EDA) 15 which in turn can communicate with a workstation 16 or server for storing the data for future reference. A disposable glove 13, also shown in FIG. 6, overlies the physician's index finger and the sensor 12.

Figure 2:
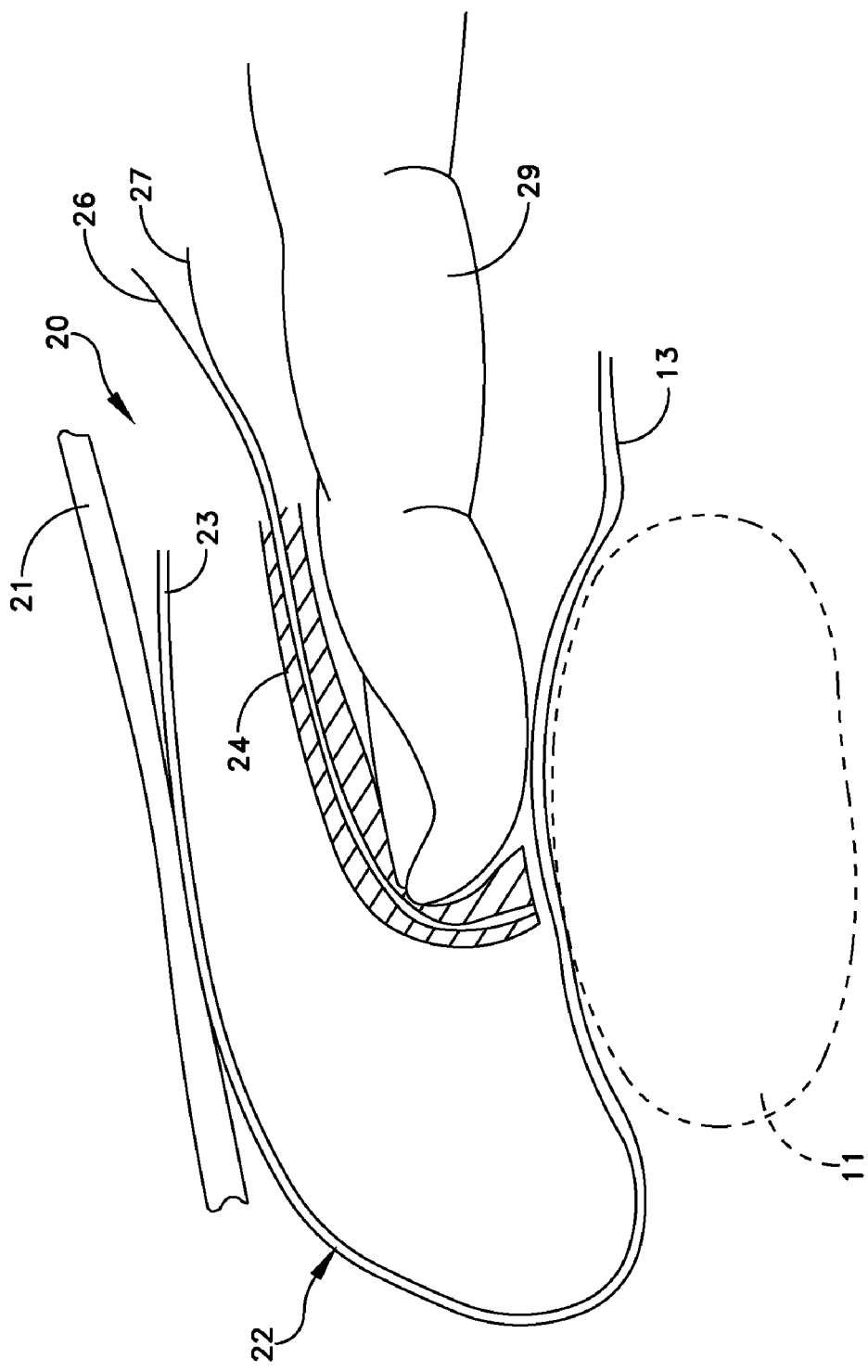
FIG. 2 shows a cross-section through a sensor and membrane shown in FIG. 1 useful in understanding this invention.
Figure 3:
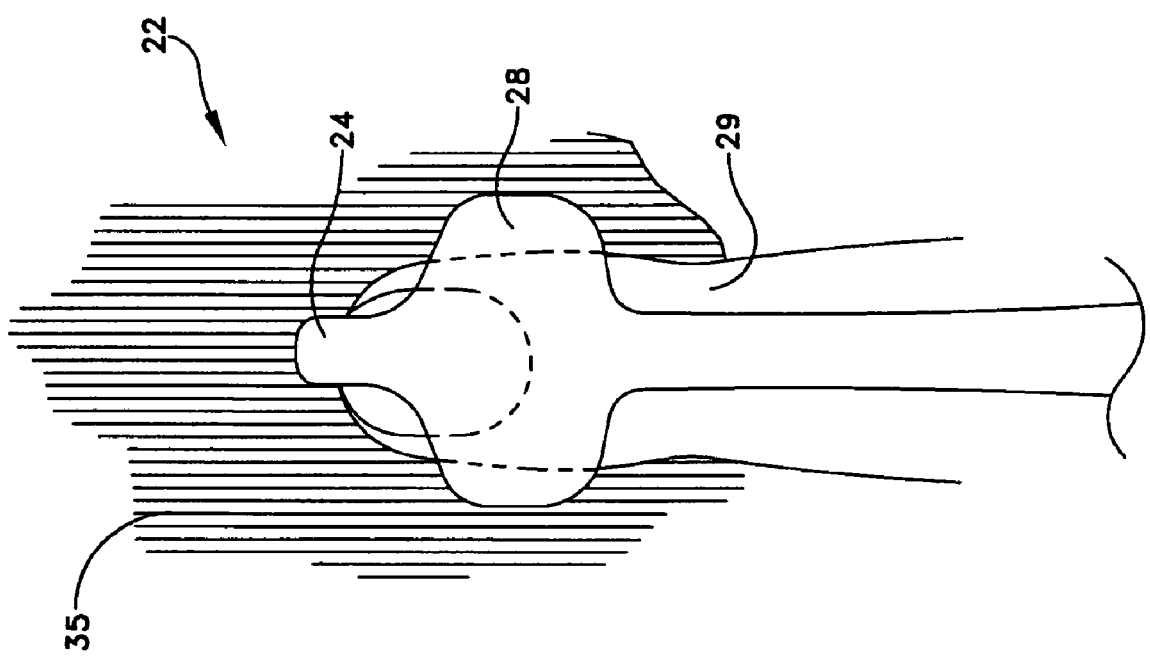
FIG. 3 is a plan view of a portion of the prostate measurement system shown in FIG. 2.
Figure 4:
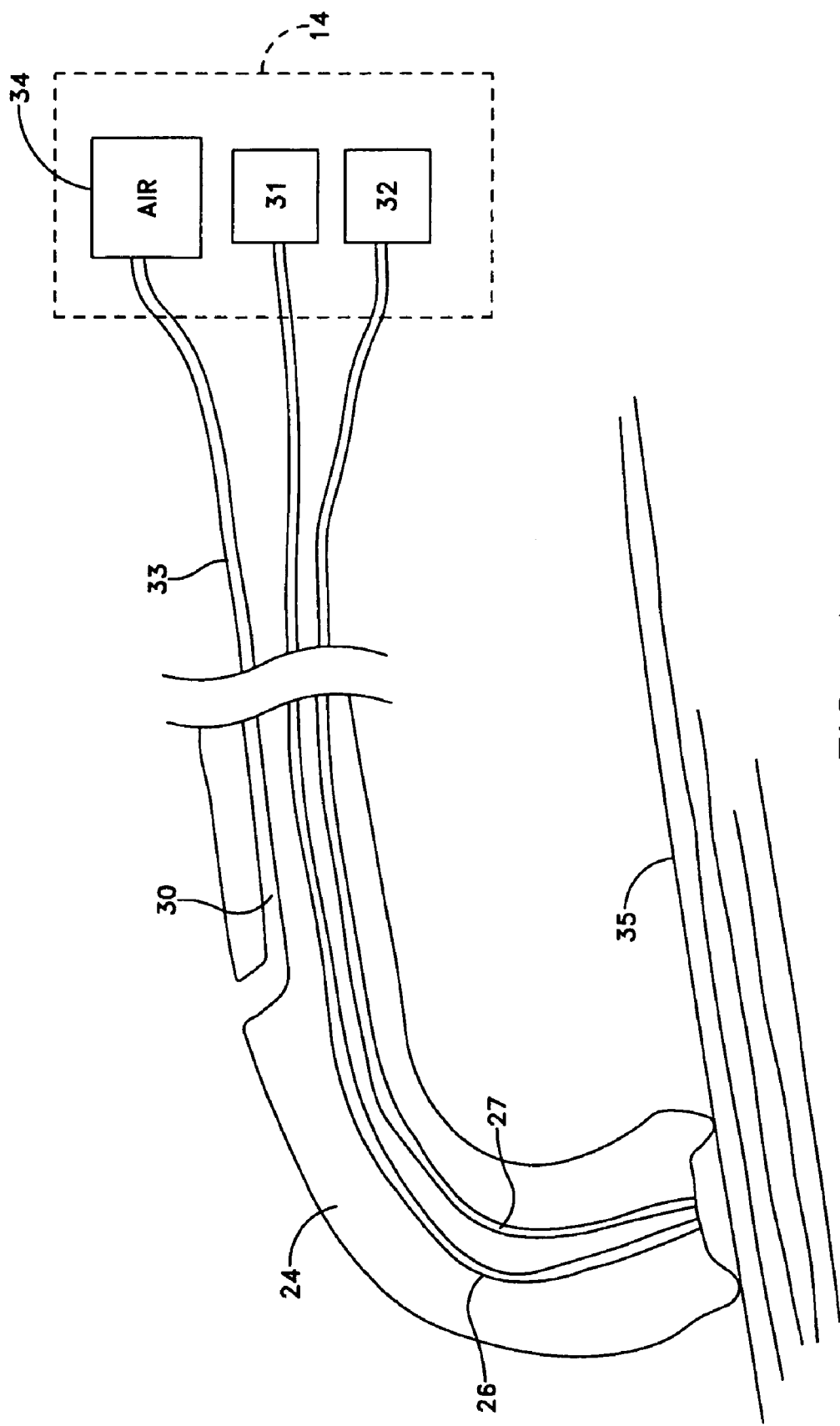
FIG. 4 is an enlarged cross-section of an index finger structure of the prostate measurement system.

Referring to FIG. 2, a patient's rectum 20 is bound by a rectum wall 21 which acts as a barrier between the rectum 20 and the prostate 11. The apparatus and method for performing an examination in accordance with this invention includes a closed membrane or sac 22 formed by a loose fitting forefinger 23 of the disposable glove 13 and a reusable index finger structure 24. As shown in FIGS. 2, 3 and 4, the index finger structure 24 is formed of a flexible material that overlies the end portion and the top of the physician's index finger. In this particular embodiment two optical fibers 26 and 27 and a passage or duct 30 are embedded in the index finger structure 24. A saddle 28 or similar clamping or attaching structure affixes the index finger structure 24 on the physician's forefinger 29.

The optical fiber 26 connects to a light source 31, generally located in the interface 14. The optical fiber 27 connects to a photodetector 32 in the interface 14. An air hose 33 connects the duct 30 to a source of low-pressure air 34.

Referring again to FIGS. 2 and 4, for an examination a physician places the index finger structure 24 on the index finger 29 and then dons the glove 13 incorporating the membrane 22 of the loose fitting forefinger 23 over the index finger structure 24. The physician inserts the index finger into the rectum and positions the membrane 22 proximate the prostate 11.

Figure 6:
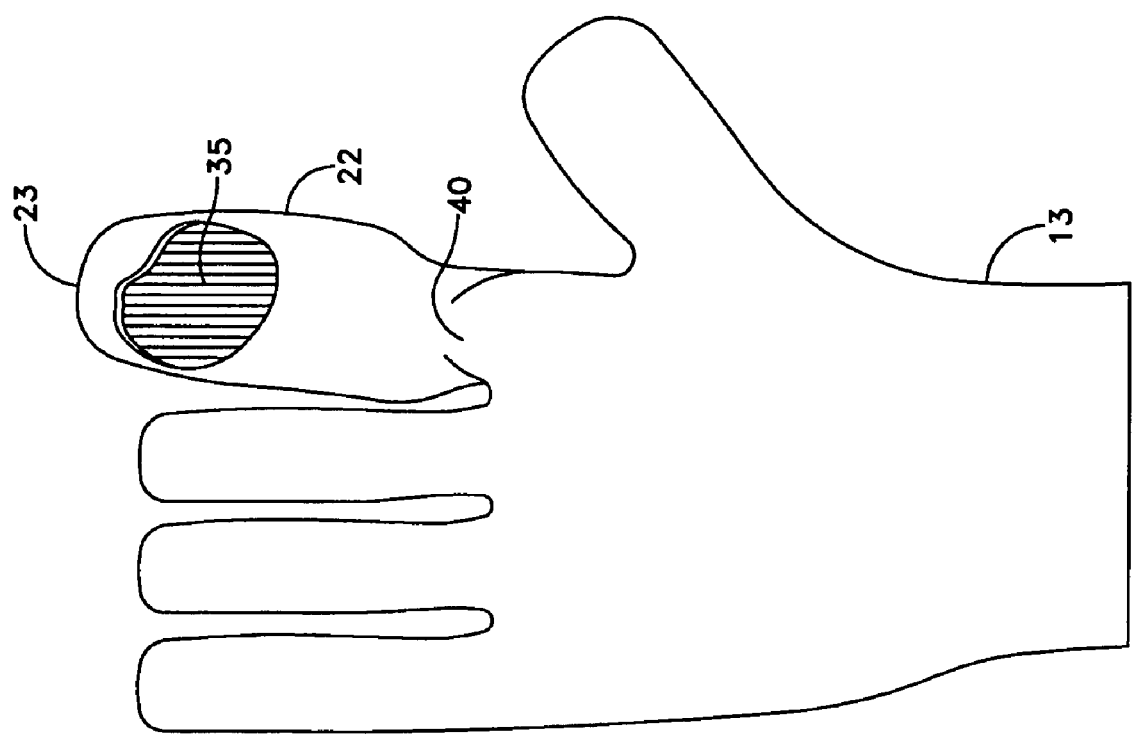
FIG. 6 is a plan view, partially broken away, of a glove useful in accordance with this invention.

Low-pressure air is then used to inflate and press the membrane 22 against the surrounding portions of the rectum wall 21 particularly in close contact with portions of the rectum wall 21 that overlie the palpable area of the prostate 11. A sealing structure 40 in the loose fitting forefinger 23, as shown in FIG. 6, confines the increased air pressure to the volume of the membrane 22. As will be apparent, when inflated, the membrane 22 defines a closed, clean volume within the rectum 20 proximate the prostate 11. Also the inflation of the membrane 22 by the air source 34 in FIG. 1 stabilizes position of the membrane 22 proximate the prostate 11.

Figure 5:
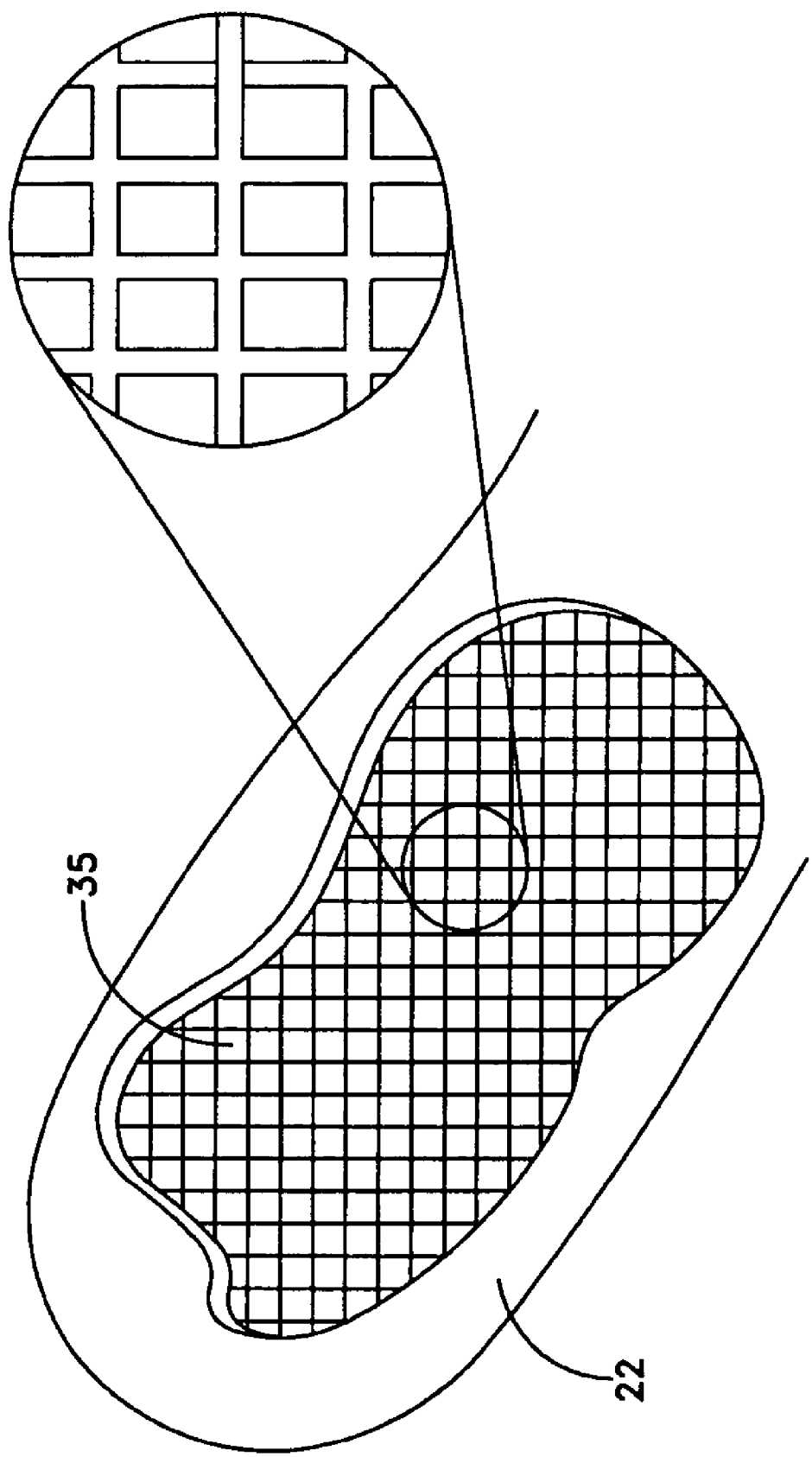
FIG. 5 is a perspective view, partially cut away, of a membrane with a grid that is useful in accordance with this invention.

Referring now to FIGS. 3 and 5, the membrane 22 includes a reference pattern in the form of a grid 35 which is visible from the interior of the membrane 22. The specific grid 35 in FIG. 3 has parallel lines printed on the interior of the membrane 22 in a contrasting color with respect to the membrane material. In this embodiment the grid defines closely spaced, alternating light and dark parallel lines approximately parallel the physician's finger to enable lateral measurement, i.e., from left to right or vice versa in FIG. 3.

As an alternate, the grid pattern could include a set of alternating dark and light lines at right angles to the set shown in FIG. 3. Still another pattern could include a combination of both sets to provide intersecting lines. Other alternative grid arrangements are also possible as, for example, a pseudo-random pattern of small dots or a pattern of connected hexagons. In any of these configurations the grid 35 provides a reference pattern over the palpable surface of the prostate.

In use, a physician determines the area of contact between the rectum wall 21 and the prostate 11. The areas where the prostate 11 separates from the rectum wall 21 are called "margins". Physicians can locate margins accurately and with good repeatability. After a physician locates one margin, the physician enables, by a switch or other means, the measurement process and moves the index finger to the opposite margin.

As the interior of the membrane 22 is clean, light reflects back from the grid to the photodetector 32 in FIG. 4 to produce displacement signals as the index finger structure 24 moves past the grid 35 thereby changing the light reflected to the photodetector 32. The PDA 15 in FIG. 1 or another equivalent device counts the number of lines in the grid that have been traversed using these displacement signals. When the physician reaches the other margin, the physician disables the system to complete the measurement. At this point the PDA 15 or other device has recorded the number of counts and may include the necessary software for providing a desired measurement of the distance traveled by the index finger structure 24 and sensor 12. This can be converted into a measurement of the size of the palpable surface of the prostate along the direction of sensor motion.

As an alternative to manual switching, the information in the signal may provide automatic delimiters on the measurement. Moreover, the PDA or related device 15 may perform all the processing that will use this information to determine the volumetric size of the prostate. Alternatively, measurements can be downloaded to a data processing system 16 for further processing and/or permanent storage.

Over time a given patient will have a series of quantitative measurements which can be reviewed by the physician. Changes in these measurements can then provide an indication concerning whether growth of the prostate is normal or abnormal.

The grid pattern on the membrane 22, such as the grid pattern 35, the light source 31 and photodetector 32 constitute one embodiment of a motion transducer that generates the displacement signals in response to the motion of the physician's index finger across the grid pattern.

An alternate means of achieving the functions of the index finger structure is to eliminate the optical fibers and attach the light source 31 and the light sensor 32 directly to the finger of the physician. In this embodiment the electrical energy for the light source 31 and the electrical signals from the photodetector 32 are connected by insulated wires to the interface circuit.

In another embodiment of the invention, the distance across the surface of the prostate is measured using a roller, ball or wheel which rolls across the surface to be measured and the distance traveled is expressed in terms of the number of degrees of rotation of the wheel or ball. The roller, ball or wheel is affixed to the end of the physician's finger and the rotation monitored by photo-electric or electromagnetic sensors.

In still another embodiment, a pattern of energizable wires or conducting filaments embedded in the thickness of the disposable glove could be substituted for the grid pattern. In this embodiment, the index finger structure would include an electrostatic or electromagnetic sensor. Alternatively, the function of the filaments and the sensor might be reversed.

In still another embodiment, the printed grid pattern could be replaced with a magnetic coating encoded by a magnetic pattern. A playback head could then be attached to the index finger structure.

Each of these embodiments provides a medical device that facilitates examinations of the prostate and the correlation of quantitative data about the size of the palpable surface of the prostate related to successive examinations of a single patient.

Repeatable quantitative measurements enable a physician to monitor prostate growth more accurately, including such parameters as rate of growth and changes in the rate of growth. Further, these measurements can be made during the course of a standard digital examination without hindering the physician's ability to obtain the subjective information about the prostate that the physician normally obtains.

The combination of the membrane and index finger structure permit measurement in a closed volume so that the measurement is made in an isolated volume. This permits the measurement to be made efficiently. Further, it will be apparent that the specifically disclosed embodiments can be readily manufactured using standard techniques.

As will now also be apparent, this invention can be implemented in a variety of configurations. Each of the foregoing or other modifications could be made while attaining some or all of the advantages of this invention. Thus it is the intent of the appended claims to cover all such variations and modifications as come within the true spirit and scope of this invention.

What is claimed as new and desired to be secured by Letters Patent of the United States is:

The invention claimed is:

1. A medical device for use by a physician for making a measurement of the size of the palpable surface of a prostate during a digital rectal examination comprising:
   A) index finger means for attachment to the end of the physician's index finger,
   B) membrane means overlying the physician's index finger with said attached index finger means for forming a closed volume proximate the prostate,
   C) stabilizing means for stabilizing the position of said membrane means with respect to the prostate,
   D) motion transducer means attached to said index finger means and to said membrane means for generating displacement signals in response to motion of the physician's index finger relative to said stabilized membrane means during palpitation of the prostate, and
   E) processing means for converting the displacement signals from said motion transducer means to data representative of the size of the palpable surface of the prostate.

2. A medical device as recited in claim 1 wherein said motion transducer means includes first means for forming a reference pattern and second means for generating displacement signals during relative motion of said second means relative to said first means during the palpation, one of said first and second means being on said membrane and the other of said first and second means being on said index finger means.

3. A medical device as recited in claim 2 wherein said first means includes a reference pattern visible from within said closed membrane means and said second means is on said index finger means and includes means for illuminating said reference pattern and means for monitoring changes in reflection from said reference pattern thereby to produce the displacement signals.

4. A medical device as recited in claim 3 including a light source and photodetector wherein said processing means responds to signals from said photodetector, wherein said reference pattern includes a parallel-line grid formed on the interior surface of said membrane means and wherein said index finger means includes means for directing light from said light source onto said pattern and means for directing light reflected from said reference pattern to said photodetector whereby said processing means responds to changes in the reflected light from said reference pattern during motion of said index finger means within said closed volume.

5. A medical device as recited in claim 1 wherein said membrane means forms the forefinger of a glove.

6. A medical device as recited in claim 5 wherein the digital rectal examination is made by inserting the index finger, said membrane means and index finger means into the rectum, said medical device including an air source and said index finger means including means for directing air under pressure into said membrane thereby to expand and stabilize the position of the membrane in the rectum proximate the palpable surface of the prostate.

7. A medical device as recited in claim 6 wherein said glove includes sealing means in said glove for confining air from said air source to the forefinger of said glove.

8. A medical device as recited in claim 6 wherein said motion transducer means includes a first means with a reference pattern visible from within said closed membrane means and a second means is on said index finger means and includes means for illuminating said reference pattern and means for monitoring changes in reflection from said reference pattern thereby to produce the displacement signals.

9. A medical device as recited in claim 8 including a light source and photodetector and said processing means responds to signals from said photodetector, said reference pattern includes a parallel-line grid formed on the interior surface of said membrane means and said index finger means includes means for directing light from said light source onto said pattern and means for directing light reflected from said reference pattern to said photodetector whereby said processing means responds to changes in the reflected light from said reference pattern during motion of said index finger means within said closed volume.

* * * * *